United States Patent [19]
Hanna

[11] Patent Number: 5,250,062
[45] Date of Patent: Oct. 5, 1993

[54] INSTRUMENT FOR SURGICALLY CORRECTING ASTIGMATISM

[76] Inventor: Khalil Hanna, 9 rue du Temple, 75007 Paris, France

[21] Appl. No.: 810,040

[22] Filed: Dec. 19, 1991

[30] Foreign Application Priority Data

Dec. 20, 1990 [FR] France .................. 90 16011

[51] Int. Cl.⁵ .............................................. A61B 17/32
[52] U.S. Cl. ...................................... 606/166; 606/172
[58] Field of Search ......................... 606/4, 5, 161, 166, 606/167, 168, 169, 170, 172, 180; 128/898, 751, 757, 758; 604/22

[56] References Cited

U.S. PATENT DOCUMENTS

| | | | |
|---|---|---|---|
| 4,319,575 | 3/1982 | Bonte | 606/166 |
| 4,423,728 | 1/1984 | Lieberman | 128/310 |
| 4,429,696 | 2/1984 | Hanna | 606/166 |
| 4,526,171 | 7/1985 | Schachar | 606/166 |
| 4,619,259 | 10/1986 | Graybill et al. | 606/166 |
| 4,688,570 | 8/1987 | Kramer et al. | 606/172 |
| 4,815,463 | 3/1989 | Hanna | 606/166 |
| 4,985,035 | 1/1991 | Torre | 606/167 |

FOREIGN PATENT DOCUMENTS

| | | |
|---|---|---|
| 147318 | 5/1986 | European Pat. Off. . |
| 2364646 | 9/1977 | France . |
| 2242835 | 10/1991 | United Kingdom ............... 606/166 |

*Primary Examiner*—Edgar S. Burr
*Assistant Examiner*—Christopher A. Bennett
*Attorney, Agent, or Firm*—Sixbey, Friedman, Leedom & Ferguson

[57] ABSTRACT

The instrument comprises a tubular outer support forming a shell around a determined axis and including a circularly symmetrical annular base portion about the axis defining a substantially spherical annular surface enabling the support to be pressed against the cornea; the support includes a cylindrical inside wall that is resiliently deformable in the radial direction to receive the tubular top section of a template having a transverse wall at its bottom which is delimited by a substantially spherical bottom surface and which includes a central orifice and at least one pair of arcuate slots disposed symmetrically about the center of the wall.

5 Claims, 2 Drawing Sheets

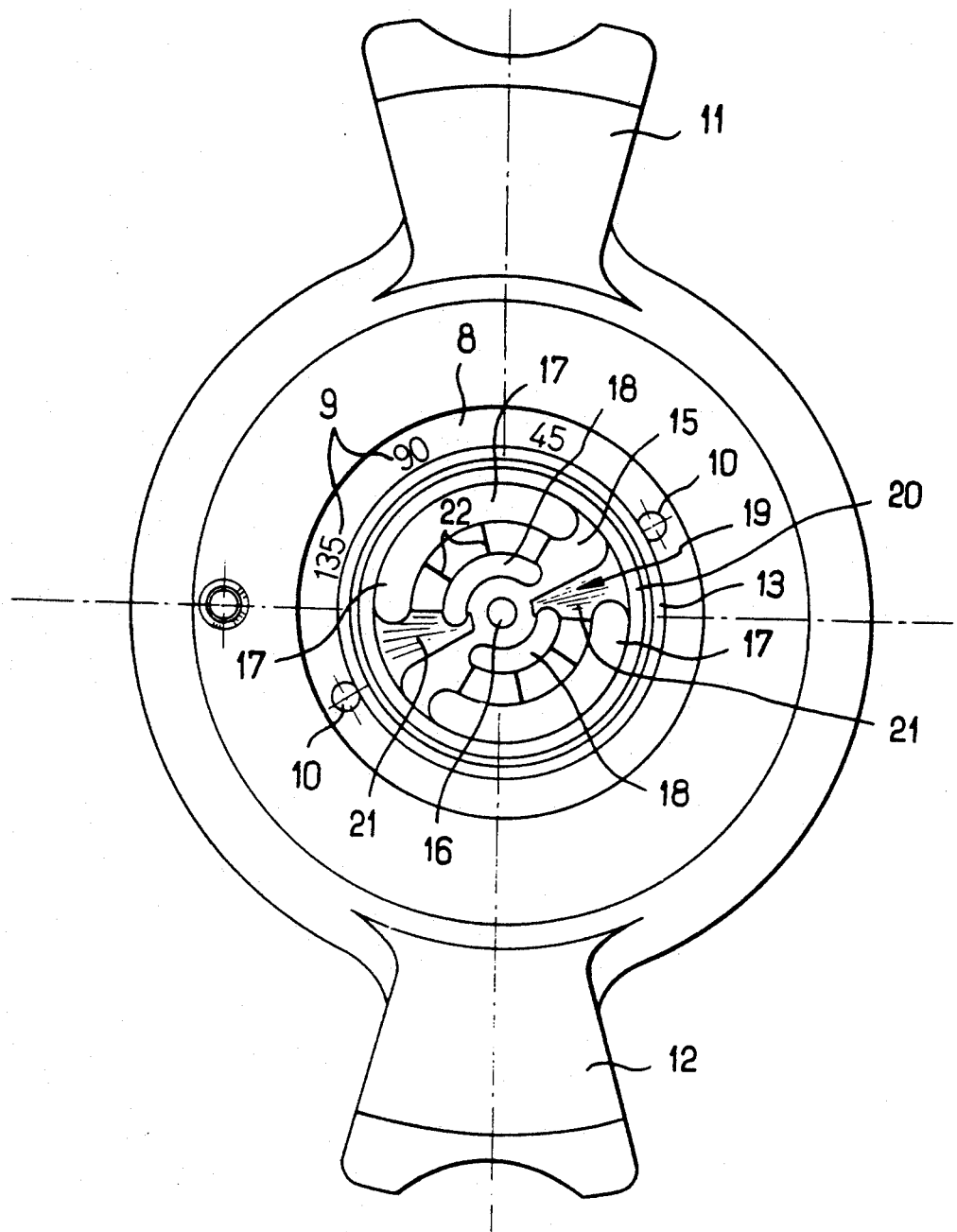
FIG_2

INSTRUMENT FOR SURGICALLY CORRECTING ASTIGMATISM

BACKGROUND OF THE INVENTION

Various specialized instruments are presently available to the surgeon for performing various cuts in the cornea as required by surgery and/or trephination of the cornea. Thus, one such keratotomy serves to make rediary incisions that are used, in particular, for correcting myopia (short sight). Another is designed to perform incisions that are transverse to a meridian of the cornea, preferably in the form of circular arcs, for the purpose of correcting astigmatism. There also exists an apparatus for trephination of the cornea for transplanting purposes.

The most common need of an ophthalmological surgeon is an instrument for surgical correction of astigmatism. This need is satisfied at present only by one of the instruments outlined above which are complicated and thus expensive and which are relatively difficult to handle.

The invention seeks to provide a much simpler instrument for making corneal incisions that are orthogonal to a meridian and that are preferably arcuate so that the incision relates to a zone of the cornea that is of substantially constant thickness. The simplicity of the instrument makes it possible to reduce the cost thereof very significantly, thereby making it available to a much larger number of practitioners.

SUMMARY OF THE INVENTION

To this end, the present invention provides an instrument for surgery of the cornea to correct astigmatism, the instrument comprising a tubular outer support forming a shell around a determined axis and including a circularly symmetrical annular base portion about the axis defining a substantially spherical annular surface enabling the support to be pressed against the cornea, wherein the support includes a cylindrical inside wall that is resiliently deformable in the radial direction to receive the tubular top section of a template having a transverse wall at its bottom which is delimited by a substantially spherical bottom surface and which includes a central orifice and at least one pair of arcuate slots disposed symmetrically about the center of the wall.

Advantageously, the template includes a mask for adjusting the angular length of the arcuate openings, the mask being constituted by a tubular sleeve mounted to rotate with friction inside the tubular section of the template and including radial wall portions at its bottom which overlie the slots to a greater or lesser extent depending on the angular position of the sleeve in the tubular section of the template.

BRIEF DESCRIPTION OF THE DRAWINGS

An embodiment of the invention is described by way of example with reference to the accompanying drawings, in which:

FIG. 2 is a plan view of the instrument.

DETAILED DESCRIPTION

Figure 1:
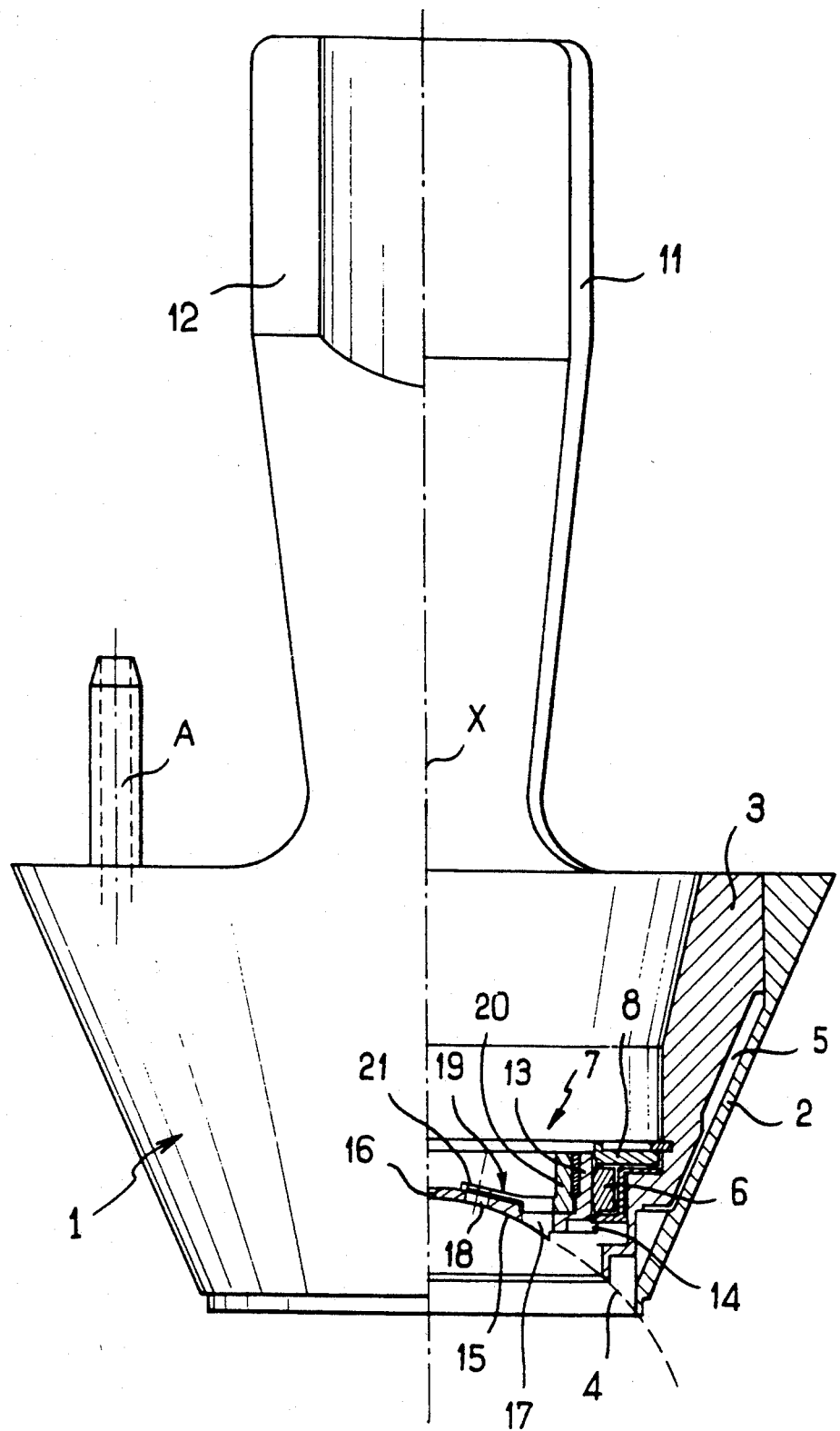
FIG. 1 is an elevation view in half-section of an instrument of the invention.

The support body 1 of the instrument shown in the figures comprises an outer shell 2 that is generally frustoconical in shape and which receives internally a complementary part 3 that is likewise frustoconical, with the two parts being coaxial about an axis X. When assembled together, these two parts define firstly a substantially spherical annular surface 4 at the base of their small diameter portion (i.e. the base portion of the support), thereby forming a surface for pressing the instrument against the sclera of the eye of a patient, and secondly they form an annular chamber 5 between each other which opens out into the surface 4. This chamber is designed to be connected by means of an endpiece A to a vacuum source whose suction enables the support to be fixed on the eye of the patient. In a simpler variant of the instrument, the support may comprise a single piece only and its base portion may include anchor claws for fixing it to the eye of a patient. In another variant, the support may include both fixing means.

The inside piece 3 of the support has a cylindrical inside sleeve 6 which is deformable radially in resilient manner, thereby enabling a guide template 7 to be fitted therein for making arcuate incisions.

Above the sleeve, the support includes a ring 8 whose top surface is engraved with angular graduations 9. This ring may be moved angularly by engaging a spike in drive orifices 10.

The support is also provided with instrument handles 11 and 12 that extend upwards parallel to the axis X of the instrument.

The template 7 includes an axial sleeve 13 with a shoulder 14 at its base to enable it to be fitted in the support. The sleeve 14 also includes a substantially spherical bottom wall 15 which is provided with a central orifice 16 and at least one pair of diametrically opposite arcuate slots. In the example shown in the figures, the spherical wall includes two pairs of slots, with the slots 17 of the first pair having a large mean diameter (e.g. 7 mm or 8 mm), while the slots 18 of the second pair have a smaller mean diameter (e.g. 5 mm or 6 mm). The angular extent of the slots is identical (about 120°). The width of the slots is equal to the width of the surgical knife that is used for making the incisions. For example, the knife may comprise a blade-carrier having a flat that defines both the width of the knife (equal to that of the arcuate slots) and the angular position of the blade.

The template further includes a moving mask 19 which is constituted by a cylindrical tubular portion 20 mounted for braked rotation inside the sleeve 13 and having diametrically opposite radial fingers 21 which are parallel to the curvature of the wall 15 of the template and which are of sufficient length to extend past the inside edges of the smaller slots 18. By rotating the mask relative to the template, the fingers 21 are moved, which fingers constitute adjustable moving ends of arcuate slots. The surgeon can thus delimit the length of the incisions that are to be performed. Radial marks 22 serve to specify the selected angular length. The surgeon can then locate the middles of the arcs and place the template within the support by making said middles coincide with the selected meridian.

I claim:

1. An instrument for surgery of the cornea to correct astigmatism, the instrument comprising a template and a tubular outer support forming a shell around a predetermined axis of the instrument including a circularly symmetrical annular base portion about the axis defining a substantially spherical annular surface for contacting the cornea, said support including a resiliently deformable cylindrical inside wall deformable in the radial direction for receiving a tubular top section of said template, said template having a substantially spherical bottom surface including a central orifice and at least one pair of arcuate slots disposed symmetrically about the central orifice.

2. An instrument according to claim 1, wherein the template includes a mask for adjusting the annular length of the arcuate openings, the mask being constituted by a tubular sleeve mounted to rotate inside the tubular section of the template and including radial wall portions at its bottom which overlie the slots and vary the exposed amount of the slots depending on the angular position of the sleeve in the tubular top section of the template.

3. An instrument according to claim 1, wherein the bottom surface includes radial marks for determining the angular length of the arcuate incisions to be made.

4. An instrument according to claim 1, wherein said template includes an annular shoulder and the resiliently deformable cylindrical inside wall is surmounted by the annular shoulder with a top surface of the annular shoulder which is substantially perpendicular to the axis including angular graduations.

5. An instrument according to claim 1, wherein the outer support includes a pair of diametrically opposite handles that are substantially parallel to a longitudinal axis of the instrument.

* * * * *